US010709581B2

(12) United States Patent
Termanini

(10) Patent No.: US 10,709,581 B2
(45) Date of Patent: Jul. 14, 2020

(54) THERMALLY SECURING MORSE TAPER

(71) Applicant: Joint Innovation Technology, LLC, Boca Raton, FL (US)

(72) Inventor: Zafer Termanini, Port Saint Lucie, FL (US)

(73) Assignee: Joint Innovation Technology LLC, Boca Raton, FL (US)

( * ) Notice: Subject to any disclaimer, the term of this patent is extended or adjusted under 35 U.S.C. 154(b) by 181 days.

(21) Appl. No.: 15/239,189

(22) Filed: Aug. 17, 2016

(65) Prior Publication Data

US 2018/0049891 A1 Feb. 22, 2018

(51) Int. Cl.
| | | |
|---|---|---|
| *A61F 2/46* | (2006.01) | |
| *A61F 2/32* | (2006.01) | |
| *A61F 2/30* | (2006.01) | |
| *A61F 2/36* | (2006.01) | |

(52) U.S. Cl.
CPC .............. *A61F 2/4637* (2013.01); *A61F 2/32* (2013.01); *A61F 2/4603* (2013.01); *A61F 2/4607* (2013.01); *A61F 2002/30332* (2013.01); *A61F 2002/30334* (2013.01); *A61F 2002/3654* (2013.01); *A61F 2002/465* (2013.01); *A61F 2002/4627* (2013.01); *A61F 2002/4628* (2013.01); *A61F 2002/4685* (2013.01)

(58) Field of Classification Search
CPC .. A61F 2/4603; A61F 2/46097; A61F 2/4637; A61F 2002/4623; A61F 2002/4624
USPC .................................. 606/99–100; 623/22.12
See application file for complete search history.

(56) References Cited

U.S. PATENT DOCUMENTS

| | | | |
|---|---|---|---|
| 4,126,924 A | 11/1978 | Akins et al. | |
| 4,644,942 A | 2/1987 | Sump | |
| 4,676,798 A * | 6/1987 | Noiles | A61F 2/32 403/135 |
| 5,133,765 A * | 7/1992 | Cuilleron | A61F 2/0095 206/363 |

(Continued)

FOREIGN PATENT DOCUMENTS

| | | |
|---|---|---|
| DE | 7601139 U1 | 5/1976 |
| DE | 8400642 U1 | 5/1984 |

(Continued)

OTHER PUBLICATIONS

International Search Report for related application PCT/US2017/046502 dated Mar. 6, 2018.

(Continued)

*Primary Examiner* — Matthew J Lawson
(74) *Attorney, Agent, or Firm* — Norris McLaughlin, PA

(57) ABSTRACT

An articular ball impactor having a heat resistant material used during "heat shrink fit" process for providing secure fixation of Morse taper components in modular orthopedic implants. The female Morse component of the articular ball is heated by electromagnetic unit providing thermal expansion. Subsequently, it is impacted over the male Morse taper component and then cooled by commonly used sterile irrigation fluid allowing the female Morse component to shrink thus providing considerable compression, fit and significant reduction of micromotion that has been so widely responsible of fretting and mechanical corrosion.

9 Claims, 4 Drawing Sheets

(56) References Cited

U.S. PATENT DOCUMENTS

| | | | | |
|---|---|---|---|---|
| 5,264,680 | A * | 11/1993 | Seibold | A61F 2/4637 |
| | | | | 219/221 |
| 7,708,739 | B2 * | 5/2010 | Kilburn | A61B 17/92 |
| | | | | 606/86 R |
| 7,807,211 | B2 | 10/2010 | Hossainy et al. | |
| 9,925,591 | B2 | 3/2018 | Eonta et al. | |
| 2003/0229357 | A1 * | 12/2003 | Dye | A61F 2/4637 |
| | | | | 606/99 |
| 2004/0117024 | A1 | 6/2004 | Gerbec et al. | |
| 2005/0209597 | A1 * | 9/2005 | Long | A61F 2/4607 |
| | | | | 606/86 R |
| 2007/0162038 | A1 * | 7/2007 | Tuke | A61F 2/4607 |
| | | | | 606/88 |
| 2007/0173948 | A1 | 7/2007 | Meridew et al. | |
| 2011/0004318 | A1 * | 1/2011 | Tulkis | A61B 17/1668 |
| | | | | 623/23.11 |
| 2014/0336776 | A1 | 11/2014 | Taylor et al. | |
| 2017/0196701 | A1 * | 7/2017 | Behzadi | A61F 2/4637 |
| 2018/0235764 | A1 * | 8/2018 | Moore | A61F 2/4014 |

FOREIGN PATENT DOCUMENTS

| | | | |
|---|---|---|---|
| FR | 2656792 | A2 | 7/1991 |
| WO | 2014074647 | A1 | 11/2013 |

OTHER PUBLICATIONS

Written Opinion of the International Search Authority for related application PCT/US2017/046502 dated Mar. 6, 2018.
Notice of References Cited in related U.S. Appl. No. 15/550,824 dated Oct. 21, 2019.

* cited by examiner

THERMALLY SECURING MORSE TAPER

FIELD OF THE INVENTION

The present invention relates generally to securing the female to male components of a Morse taper and more specifically to a heat resistant device for holding heated Morse taper orthopedic implant component.

BACKGROUND OF THE INVENTION

Thermal expansion is the tendency of matter to change in shape and volume in response to a change in temperature through heat transfer. Thermal expansion has been used in mechanical applications since early civilizations. Expansion and contraction of components by heat was widely used to fit metallic parts over one another, e.g. a metallic bushing can be fitted over a shaft by making its inner diameter slightly smaller than the diameter of the shaft, then heating it until it fits over the shaft, and allowing it to cool after it has been pushed over the shaft, thus achieving a "shrink fit". Induction shrink fitting is common industrial method to preheat metal components between 150° C. and 300° C. thereby causing them to expand and allow for the insertion or removal of another component.

Modular orthopedic implants commonly use Morse tapers for attaching its components to provide to the operating surgeon the choice of different sizes in order to fit different anatomical shapes. However modularity have been frequently incriminated in release of metal wear debris, causing local inflammatory reactions ultimately leading to osteolysis. Pain and functional disability has frequently led to extensive surgical revisions of the implants and significant clinical and functional limitation.

It has been well established in-vivo as well as in-vitro that micromotion between the male and female components of a Morse taper was major culprit in initiating "fretting corrosion". The later will damage the protective oxide layer of the contact surfaces between the taper components and initiate corrosive cascade. The presence of impurities and local tissue fluid will trigger galvanic corrosion by lowering the Ph of the interface milieu, which will release metal-hydrides ions causing further damage to the contact surface. It has been reported that manual impaction of the components was not sufficient to reduce micromotion between the components since cyclic loading of normal gait and other daily activities caused the components to cantilever and move.

Therefore, eliminating micromotion between the taper components at the level of the contact surface will significantly reduce the corrosion at multiple level of the corrosive cascade.

BRIEF DESCRIPTION OF THE INVENTION

To achieve this goal, the present invention provides a method for significantly reducing corrosion between the contact surfaces of Morse taper by eliminating "micromotion" between the impacted components. Using the mechanical application of thermal expansion, "shrink fit" is induced between the components to provide considerable contact pressure that exceed load generated by manual impaction. The female component is heated and impacted over the male component of the taper then cooled by cold sterile irrigation fluid, readily available in operating rooms, thus providing considerable contact pressure between the two components.

It is however imperative to protect the surrounding tissues from the heated female component to avoid burns. The present invention describes a device comprising a heat resistant impactor having a protective heat shield skirt that will hold the heated female component but keep the surrounding tissues away and prevent them from coining in contact with the heated component.

The general purpose of the present invention, which will be described subsequently in greater detail, is to provide a novice heat protective impactor of the female component of a Morse taper.

This novel feature is not anticipated, rendered obvious, suggested or even implied by any prior art, either alone or in any combination thereof. To attain this, the present invention generally comprises a metallic impactor handle having a heat resistant distal protective skirt providing protection of the heated component from coining in contact with the surrounding tissues of the surgical wound. Furthermore, spring loaded retaining claws will firmly hold the heated component, such as the femoral/acetabular ball during insertion but easily release said component by simply pressing the releasing levers.

There are additional features of the invention that will be described hereinafter. In the respect, before explaining at least one embodiment of the invention in details, it is to be understood that the invention is not limited in its application to the details of construction and to the arrangement of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

To the accomplishment of the above described and related objects, this invention may be embodied in the form illustrated in the accompanying drawings, attention being called to the fact, however, that the drawings are merely illustrative and that changes may be made in the specific construction illustrated.

BRIEF DESCRIPTION OF THE DRAWINGS

Various other objects, features and attendant advantages of the present invention will become fully appreciated as the same becomes better understood wen considered in conjunction with the accompanying drawings, in which like references characters designate the same or similar parts throughout the several views, and wherein.

DETAILED DESCRIPTION OF THR DRAWINGS

Figure 1:
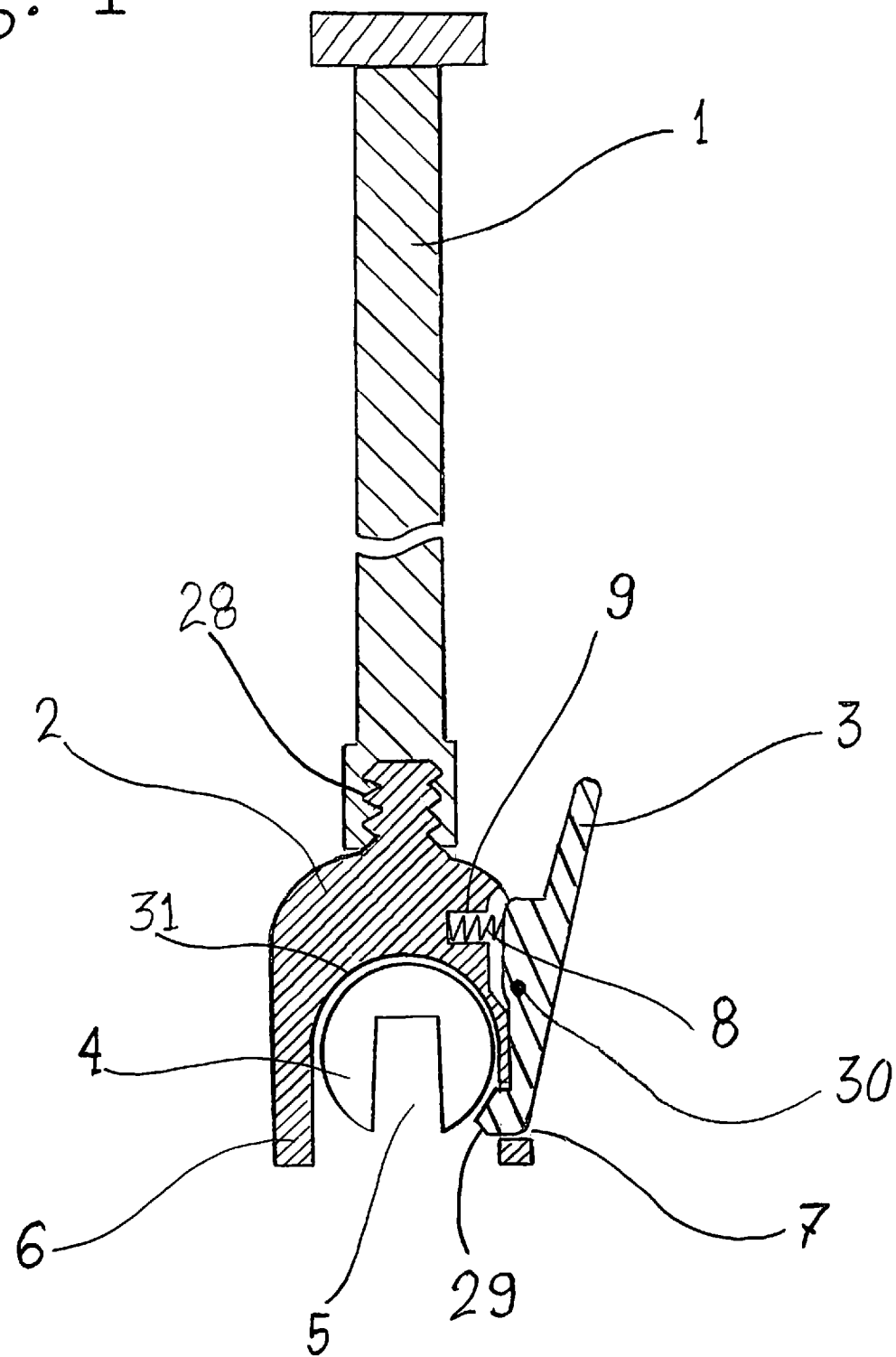
FIG. 1 is a cross sectional view of the impactor/holder of the articular ball.
Figure 2:
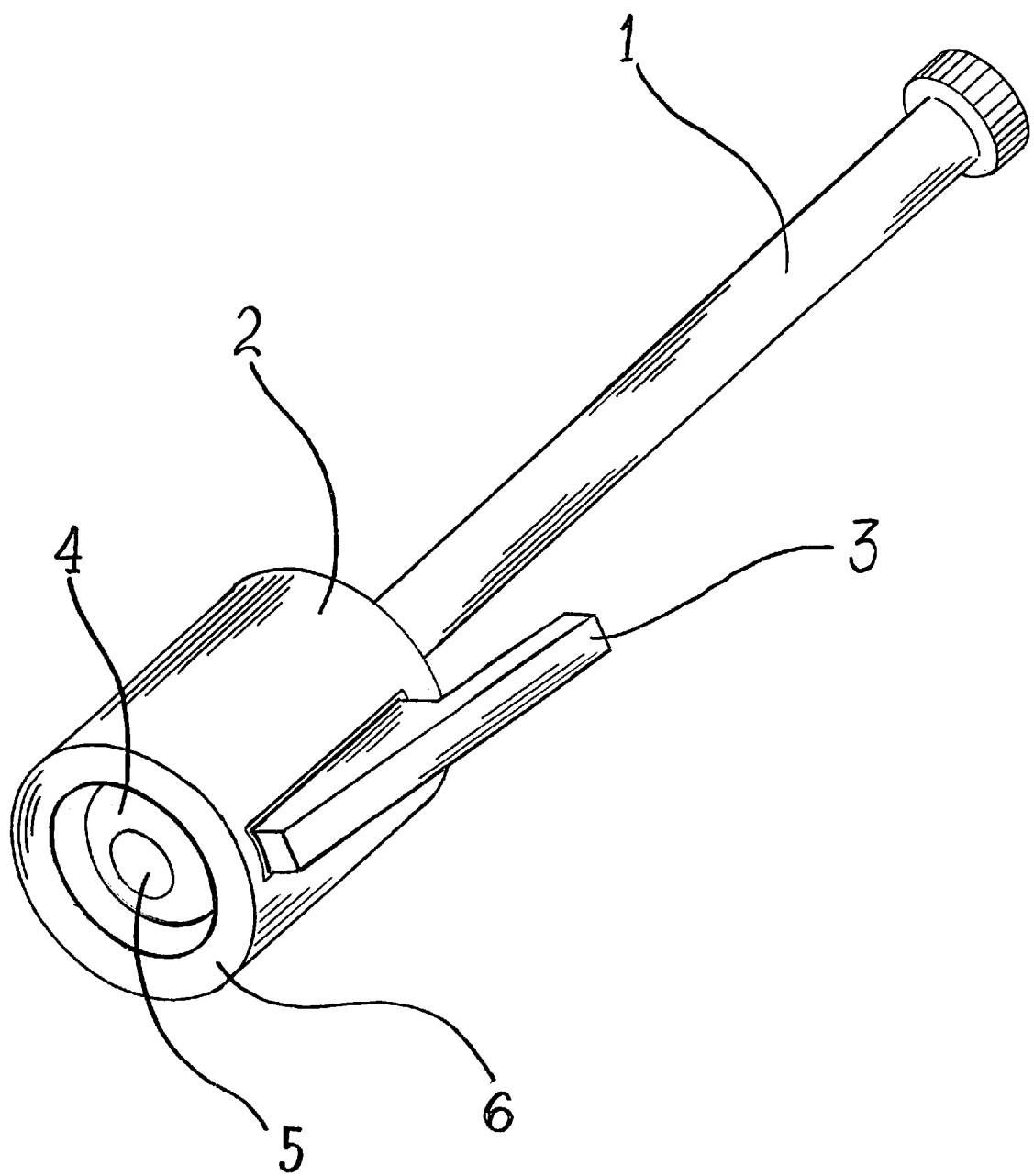
FIG. 2 is a perspective view of the impactor/holder revealing the release lever.

Turning now descriptively to the drawings, in which similar references characters denote similar elements throughout the several views, the attached figures illustrate a metallic impactor handle 1, which is attached distally to a cylindrically shaped heat resistant impactor body 2 (FIG. 1), which is screwed proximally into the distal end of the metallic handle shaft and secured by threads 28. The impactor body 2 extends distally to form a protective circular thermal skirt 6. Said impactor body 2 comprises a round cavity 31 which will receive an articular metallic ball 4, which comprises a cylindrical female Morse cavity 5.

The impactor body and the extended skirt are fabricated from heat resistant material that withstands temperatures in excess of 275° C. without deformation or melting. Materials may include resins, composites, ceramics, or fiberglass or combination thereof. To keep the ball secured inside the impactor cavity after heating, a lever 3 having a claw 29 is situated on the side of the impactor body and secured by pin 30. Spring 8 located inside cylindrical cavity 9 will keep the claw under tension inside opening 7. Additional lever on the opposite side may also be provided for further securing the heated ball.

Figure 3:
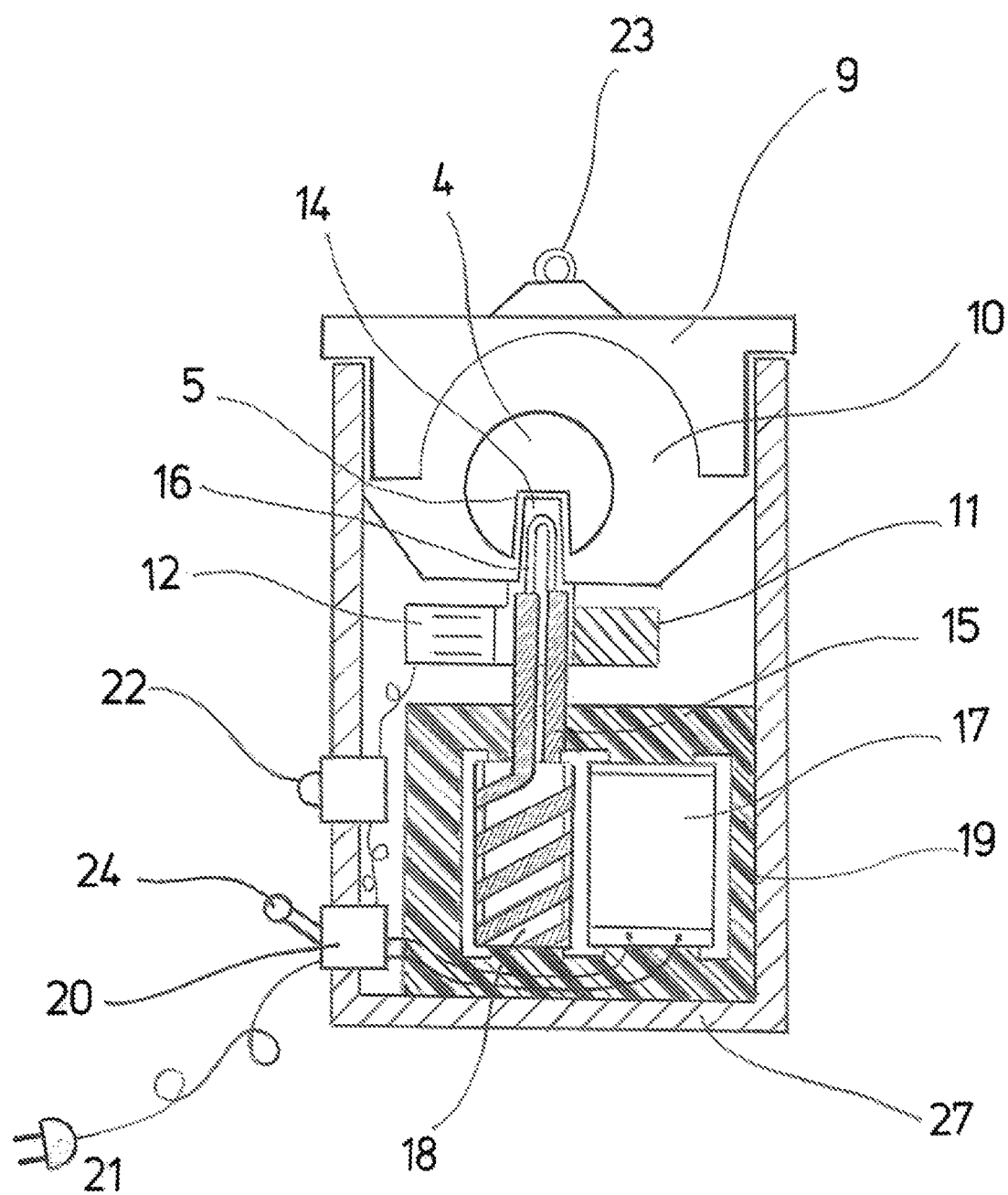
FIG. 3 is across sectional view of the articular ball electromagnetic heater.

To provide thermal expansion to the articular ball implant, heating is performed by using electromagnetic unit that will provide dry heat (FIG. 3). Said unit is encased in enclosure 27. A primary electromagnetic coil 17 wrapped around iron core 19 will generate powerful current in secondary coil 18 which will be conveyed by large electrical conduit cable 15 and connect with heating element 16. Said heating element is situated inside heating core 14 having the form of a male taper, which will slidingly accept the female taper 5 of the articular ball implant 4. The male taper being non-conform to avoid binding between the two components.

Once the articular ball in inserted onto the heating core, the heating chamber 10 is covered with lid 9 to avoid heat dissipation. The heating is turned on by switch 24 and control unit 20 will activate the primary coil, which in turn will generate significant current output through the secondary coil 18. Said current is transmitted through the thermal base 11 to the heating element 16. Subsequently, the heating element will start to warm up to reach a temperature between 280° and 400° F.

Establishing vacuum in the heating chamber through vacuum valve 32 may significantly increase the heating process, especially when large implants are heated. Insertion of inert or rare gases may also improve the heat transfer.

A variable closed circuit thermostat 12 is used to control the temperature by controlling duration needed to reach the required temperature. Different temperature setting is needed for different size components. Visual aids such as light 22 and beeps will alert the operator that heating process has reached the desired temperature. The power distributor 20 will then turn off electric current to the primary coil and the articular ball implant has reached the desired thermal expansion and ready to be removed from the heating chamber.

To remove the extremely hot ball the heat resistant impactor and skirt is used. The protective lid is removed and the impactor is then seated on top of the articular ball until the claw snaps around the ball. The implant is then promptly removed from the heating unit and brought by the operating surgeon to the surgical wound and seated onto the implant where the female taper opening is slidingly inserted onto the male taper.

Once the ball implant is seated properly, it is then impacted using conventional mallet. The heat resistant skirt, which extends beyond the ball, will keep surrounding tissues from contacting the hot articular ball.

After completing the impaction of the ball, the impactor is kept in place for providing continuous thermal protection. The "shrink fit" is accomplished by cooling the articular ball using cooled irrigation fluid commonly used and readily available in operating rooms. The impactor is then removed and further cooling is continued using irrigation fluid. In view of the high temperature, the ball as well as the heating chamber become sterilized from any living material including germs and viruses.

Figure 4:
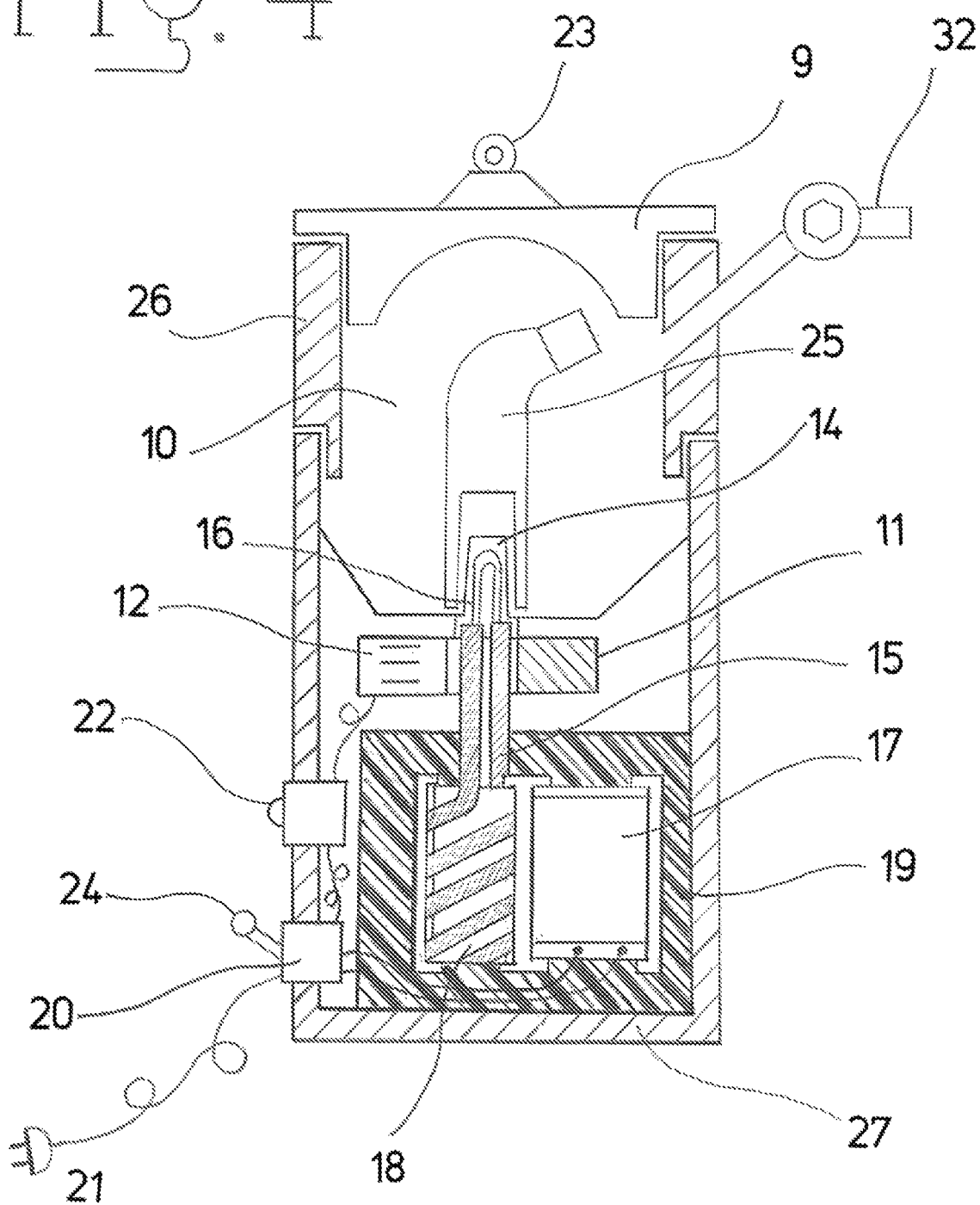
FIG. 4 is a cross sectional view of the electromagnetic heater having a top extension for using larger orthopedic taper components.

A variation of the present invention may include a different embodiment where the above described articular ball implant my be replaced by a different larger implant such as a revision proximal femoral implant having Morse taper. The heating chamber need to be extended and extension 26 will the be used as depicted in FIG. 4. In view of the increased mass, different heat setting and heating time will be set in order to accomplish the appropriate thermal expansion.

As to a further discussion of the manner of usage and operation of the present invention, the same should be apparent from the above description. With respect to the above description then, it is to be realized that the optimum dimensional relationships for the parts of the invention, to include variation in size, material, shape, form, function and manner of operation, assembly and use, are readily apparent and obvious to one skilled in the art and all equivalent relationships to those illustrated in the drawings and described in the specification are intended to be encompassed by the present invention. Therefore, the foregoing is considered as illustrative only of the principles of the invention.

Other means to heat the articular ball are available in the industry such as Radiofrequency emitters similar to microwave. However, these devices may interfere with medical monitoring devices causing hazard thus not safe in hospital setting.

Furthermore, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed:

1. An orthopedic device assembly including a part configured to removably hold a heated articular ball of an orthopedic prosthesis, the ball having a tapered cavity extending into the interior thereof configured for the receipt of a correspondingly configured male part of a further part of the orthopedic device, the part comprising:
   an upper metallic handle shaft,
   a lower cylindrical impactor body having a round bottom and which includes a spring loaded retaining lever having a claw adapted to hold the heated articular ball within the cylinder and which retains the ball within the said body until the spring is compressed and the claw disengages the said ball, the said body screwed to said handle shaft configured to removably hold the heated articular ball having a temperature of at least 280° C., the heated articular ball having a female component, and wherein the impactor body comprises a rigid, thermally insulating material or a deformable thermally insulating material which contacts the heated articular ball, and
   a protective circular thermal skirt adapted to keep surrounding tissues away from the heated articular ball when held within the circular thermal skirt.

2. The assembly of claim 1, wherein the protective circular thermal skirt is formed from a material selected from: resins, composites, ceramics, fiberglass, and combinations thereof.

3. The assembly of claim 1, wherein the tapered cavity is a female Morse taper.

4. An orthopedic device assembly adapted for removably retaining a heated component of an orthopedic prosthesis the component having a tapered cavity configured for the receipt of a correspondingly configured male part of an orthopedic device, the orthopedic device assembly comprising:
   an upper metallic handle shaft,
   a lower cylindrical impactor body having a round bottom and which includes a spring loaded retaining lever having a claw adapted to hold the heated articular ball within the cylinder and which retains the ball within the said body until the spring is compressed and the claw disengages the said ball, the said body screwed to said handle shaft configured to removably hold the heated articular ball having a temperature of at least 280° C., the heated articular ball having the tapered cavity, and
a protective circular thermal skirt adapted to keep surrounding tissues away from and insulated from the heated component retained within the circular thermal skirt.

5. The orthopedic device assembly of claim 4, wherein the circular thermal skirt is formed from a material selected from: resins, composites, ceramics, fiberglass, and combinations thereof.

6. The orthopedic device assembly of claim 4, wherein the lower cylindrical impactor body is a circular thermal skirt formed from a material selected from: resins, composites, ceramics, fiberglass, and combinations thereof.

7. The orthopedic device assembly of claim 4, wherein the spring, the lever and claw are situated on a side of the impactor body.

8. The orthopedic device assembly of claim 4, wherein the orthopedic implant is an articular ball having a female component.

9. The orthopedic device assembly of claim 8, wherein the female component is a Morse taper.

* * * * *